United States Patent [19]

Fischer et al.

[11] 4,028,402
[45] June 7, 1977

[54] BIGUANIDE SALTS

[75] Inventors: Ulf Fischer, Frenkendorf; Eckehard Lorch, Reinach, both of Switzerland

[73] Assignee: Hoffmann-La Roche Inc., Nutley, N.J.

[22] Filed: Oct. 8, 1975

[21] Appl. No.: 620,525

[30] Foreign Application Priority Data

Oct. 11, 1974 Switzerland .................... 13697/74

[52] U.S. Cl. .......................... 260/501.14; 424/199; 424/316; 424/212; 424/267; 424/274; 424/244; 260/502.5; 260/239 A; 260/239 E; 260/239 BF; 260/293.65; 260/293.87; 260/941
[51] Int. Cl.² ........................ C07C 129/16
[58] Field of Search .................. 260/501.14

[56] References Cited

UNITED STATES PATENTS 3,179,562 4/1965 Hoffman et al. ............... 260/501.1

OTHER PUBLICATIONS

Osterloh, Chem. Abstracts, vol. 56, 13504(a) 1962.
Ueda, Chem. Abstracts, vol. 61, 11900(h) 1964.
Paul et al., Chem. Abstracts, vol. 59, 9872(d) 1963.
Schillinger et al., Chem. Abstracts, vol. 77, 160056r, 1972.
Skillman, Chem. Abstracts, vol. 78, 119019(p) (1973).
Hellmut et al., Chem. Abstracts, 11q, vol. 78, (1973).

*Primary Examiner*—Bernard Helfin
*Assistant Examiner*—G. T. Breitenstein
*Attorney, Agent, or Firm*—Samuel L. Welt; Bernard S. Leon; William G. Isgro

[57] ABSTRACT

Biguanide salts of the formula

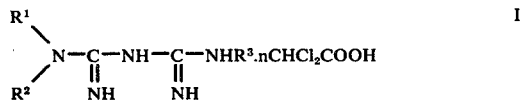

wherein $R^1$, $R^2$, $R^3$ and $n$ are as hereinafter set forth, are described. The aforementioned biguanides are useful as hypoglycemic agents.

5 Claims, No Drawings

BIGUANIDE SALTS

BRIEF SUMMARY OF THE INVENTION

The invention relates to biguanides of the formula

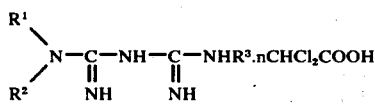

wherein $R^1$ is hydrogen, lower alkyl or lower alkenyl; $R^2$ is lower alkyl, aryl, aryl-lower alkyl, or aryloxy-lower alkyl; or $R^1$ and $R^2$, taken together, are lower alkylene; $R^3$ is hydrogen or a residue of the formula

wherein $R^4$ and $R^5$ are hydrogen or a cation, or $R^4$ is hydrogen and $R^5$ is lower alkyl, or $R^4$ and $R^5$, taken together, are lower alkylene; and $n$ is 1 or 2.

DETAILED DESCRIPTION OF THE INVENTION

The invention relates to biguanide salts. In another aspect, the invention relates to pharmaceutical preparations which contain the aforementioned biguanide salts. The biguanide salts of the invention are characterized by the formula

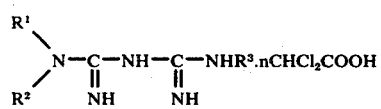

wherein $R^1$ is hydrogen, lower alkyl or lower alkenyl; $R^2$ is lower alkyl, aryl, aryl-lower alkyl, or aryloxy-lower alkyl; or $R^1$ and $R^2$, taken together, are lower alkylene; $R^3$ is hydrogen or a residue of the formula

wherein $R^4$ and $R^5$ are hydrogen or a cation, or $R^4$ is hydrogen and $R^5$ is lower alkyl, or $R^4$ and $R^5$, taken together, are lower alkylene; and $n$ is 1 to 2.

As used herein, the term "lower alkyl" denotes an alkyl group of 1-7 carbon atoms, for example, methyl, ethyl, propyl, isopropyl, butyl, isomers thereof, and the like. The term "lower alkenyl" denotes an alkenyl group of 2-7 carbon atoms, for example, vinyl, allyl and the like. The term "aryl" denotes as aromatic hydrocarbon radical, for example, phenyl, which may contain one or more substituents, such as, for example, lower alkyl, lower alkoxy and halogen. Halogen denotes chlorine, bromine, fluorine, and iodine; preferably chlorine. As used herein, the term "cation" denotes a cation such as, $Na^+$, $K^+$ or $NH_4^+$; $Ca^{++}$, $Mg^{++}$. The term "lower alkylene" denotes as alkylene group having 2-7 carbon atoms such as ethylene, trimethylene, tetramethylene and penta methylene.

Compounds of formula I wherein $R_1$ is hydrogen or lower alkyl, $R^2$ is lower alkyl or phenyl-lower alkyl and $R^3$ is hydrogen are preferred.

Examples of the compounds of formula I are:

1-phenethylbiguanide mono-dichloroacetate,
1-phenethylbiguanide bis-dichloroacetate,
1-n-butylbiguanide mono-dichloroacetate,
1-n-butylbiguanide bis-dichloroacetate,
1,1-dimethylbiguanide mono-dichloroacetate,
1,1-dimethylbiguanide bis-dichloroacetate,
1-pentylbiguanide mono-dichloroacetate,
1-pentylbiguanide bis-dichloroacetate,
1-isopentylbiguanide mono-dichloroacetate,
1-isopentylbiguanide bis-dichloroacetate,
1-benzyl-1-methylbiguanide mono-dichloroacetate,
1-benzyl-1-methylbiguanide bis-dichloroacetate,
1-benzyl-5-phosphorylbiguanide (benfosformin) mono di-chloroacetate, or the like.

The biguanide salts of formula I can be prepared in a known manner for preparing salts from the corresponding bases, i.e., by reaction of the corresponding biguanide with dichloroacetic acid or by double decomposition of salts, i.e., by reaction of a biguanide salt of an acid other than dichloroacetic acid with a dichloroacetate compound.

In a preferred embodiment, a biguanide salt of a mineral acid, e.g., the hydrochloride, the nitrate or sulfate is reacted with an alkali metal dichloroacetate, for example, sodium, potassium or ammonium dichloroacetate or with calcium dichloroacetate and dichloroacetic acid in a medium in which the alkali salt of the mineral acid is poorly soluble. Solvents such as ethanol, acetone, dioxane, acetonitrile, isopropanol, or the like, and in particular, ethylacetate, may be utilized in the aforementioned embodiment.

The desired biguanide salt of formula I can be isolated by means of known procedures, for example, by concentration of the solution obtained after separation of the precipitated mineral salt and subsequent crystallization.

Depending on the stoichiometric ratios of the reactants, the mono- or the bis-dichloroacetate of the biguanide employed as the starting material is obtained. The mono-dichloroacetates can also be obtained from the bis-dichloroacetates by cleavage of dichloroacetic acid. The cleavage can be effected, for example, by heating under reduced pressure.

The biguanide salts of formula I are useful for the treatment of metabolic disorders. More particularly, the biguanide salts of formula I are useful as hypoglycemic agents, for example, are useful in the treatment of Diabetes mellitus.

As is well known, the treatment of Diabetes mellitus with biguanides leads to undesired side effects, for example, to a lactate accumulation [hyperlactatemia; c.f. Brit. Med. J. 5794/I, 205–206, (1972) ]. Under certain conditions, this can lead to a lacetacidosis [Acta Med. Scand. 191, 203–208 (1972) ].

It has now been found that the biguanide salts of formula I of the invention effect a lowering of the blood sugar level at least comparable to the known biguanides, without the aforementioned disadvantage of the lactate accumulation. The advantageous effect which can be produced with the biguanide salts of the invention is evident from the following test results:

TABLE I

The desirable action of a single oral dose of n-butylbiguanide and of n-butylbiguanide bis-dichloroacetate on the concentration of the blood glucose and the blood lactate in Streptozotocin-diabetic rats which have been refed after a previous period of staration, was demonstrated by the method and results hereinafter described.

|  | Dose (μmol/kg) | Blood glucose % in controls | Blood lactate % in controls |
|---|---|---|---|
| Controls | — | 100 | 100 |
| Hydrochloride of | 100 | 76** | 123* |
| n-butylbiguanide | 300 | 68** | 114* |
|  | 1000 | 35*** | 254*** |
| Bis-dichloroacetate | 100 | 69*** | 91 |
| of n-butylbiguanide | 300 | 62*** | 100 |
|  | 1000 | 37*** | 106 |

*: $p < 0.1$
**: $p < 0.01$
***: $p < 0.001$
Significance of the > deviations from controls Female albino rats (130–150 g.), which have been treated for 3 weeks before the test with Streptozotocin (60 mg/kg. s.c.), were fasted (24 hours) and subsequently refed for 16 hours. The test substances were administered to groups of six rats each as a suspension in 5% gum arabic by means of a probang. Controls received the same volume of the carrier suspension alone (10 ml/kg). Four hours after administration of the test substances, the animals were decapitated. After deproteinization of the mixed blood with perchloric acid, glucose concentration was determined photometrically by the hexokinase method. Lactate concentration was determined photometrically with lactate dehydrogenase.

TABLE II

The desirable action of 3 or 5 oral doses of biguanide hydrochlorides and biguanide dis-dichloroacetates on the concentration of lactate in the blood of normal, fasted rats, was demonstrated by the method and results hereinafter described.

|  | Number of Doses | Dose (μmol/kg) | Hours after the Last Dose | |
|---|---|---|---|---|
|  |  |  | 1 % of Controls | 4 % of Controls |
| Controls | — | — | 100 | 100 |
| n-butylbiguanide hydrochloride | 3 | 450 | 236*** | 230*** |
|  | 5 | 450 | 480*** | 582*** |
| Phenethylbiguanide hydrochloride | 3 | 2500 | 182*** | 151 |
| Dimethylbiguanide hydrochloride | 3 | 7000 | 403*** | 278*** |
| n-butylbiguanide bis-dichloroacetate | 3 | 450 | 130° | 160° |
|  | 5 | 450 | 99 | 104 |
| Phenethylbiguanide bis-dichloroacetate | 3 | 2500 | 63*** | 63* |
| Dimethylbiguanide bis-dichloroacetate | 3 | 7000 | 41*** | — |

°: $< 0.1$
*: $< 0.05$
**: $< 0.01$
***: $< 0.001$
> Significance of the deviations from controls The test substances were administered to groups of male albino rats (130–150 g.) as a suspension in 5% gum arabic by means of a probang. Controls received the same volume of the carrier suspension alone. Feeding was terminated with the first administration. One and four hours after the last administration, the animals were decapitated, the mixed blood deproteinized (perchloric acid). Lactate concentration was determined photometrically in the protein-free supernatant by means of lactate dehydrogenase.

TABLE III

The biguanide salts of formula I also showed favorable properties in the toxicological testing. $LD_{50}$'s obtained with single daily oral administration of the test substance for 10 days, 24 hours after the last administration, are set forth below:

|  | mmol/kg | |
|---|---|---|
|  | Mouse | Rat |
| n-Butylbiguanide bis-dichloroacetate | 1.13 ± 0.18 | 1.20 ± 0.20 |
| Phenethylbiguanide bis-dichloroacetate | 1.61 ± 0.26 | 2.90 ± 0.46 |
| n-Butylbiguanide hydrochloride | 1.37 ± 0.22 | 0.66 ± 0.10 |
| Phenethylbiguanide hydrochloride | 0.69 ± 0.11 | 3.60 ± 0.58 |

The biguanide salts of formula I are useful as agents for the treatment of diabetes. The dosage utilized for such treatment, corresponds, calculated on a similar basis, to the dosage of the corresponding biguanides or their hydrochlorides.

The biguanide salts of formula I can be utilized in the form of pharmaceutical preparations which contain them in admixture with the usual pharmaceutical adjuvant materials, such as organic or inorganic, inert carriers, for example, water, gelatin, lactose, starch, magnesium stearate, talc, and the like. The pharmaceutical preparations can comprise, for example, tablets, dragees, suppositories, capsules. The pharmaceutical adjuvant materials can include preservatives, stabilizers, or the like. They can also contain other therapeutically active materials.

The following Examples further illustrate the invention. All temperatures are in degrees Centigrade, unless otherwise mentioned.

EXAMPLE 1

Preparation of 1,1-dimethylbiguanide bis-(dichloroacetate)

109.5 G. of 1,1-dimethylbiguanide .HCl, 100.0 g. of sodium dichloroacetate and 214.0 g. of dichloroacetic acid were boiled together in 3.5 l. of absolute ethyl acetate at reflux for 1 hour. The hot solution was filtered through Speedex under suction in order to separate the precipitated sodium chloride. From the filtrate, there crystallizes on cooling 1,1-dimethylbiguanide bis-(dichloroacetate) analysis pure. M.P.: 116°–117° C.

With longer drying in vacuo at 100° C., the bis-(dichloroacetate) loses 1 mole of dichloroacetic acid, whereby there is obtained by crystalline 1,1-dimethylbiguanide dichloroacetate. M.P.: 160°–161.5° C.

EXAMPLE 2

Preparation of 1-phenethylbiguanide bis-(dichloroacetate)

161.0 G. of 1-phenethylbiguanide.HCl, 101.0 g. of sodium dichloroacetae and 216.0 g. of dichloroacetic acid were boiled together in 4.5 l. of absolute ethyl acetate at reflux for 1 hour. The hot solution was filtered under suction in order to separate the precipitated sodium chloride. The filtrate was concentrated in vacuo and treated with diisopropylether, whereby 1-phenethylbiguanide bis-(dichloroacetate) crystallized out analytically pure, M.P.: 131°–132° C.

EXAMPLE 3

Preparation of pure 1-butylbiguanide bis-(dichloroacetate)

150.0 g. of 1-butylbiguanide.HCl, 117.0 g. of sodium dichloroacetate and 250.0 g. of dichloroacetic acid were boiled together in 4.5 l. of absolute ethyl acetate at reflux for 1 hour. The hot solution was filtered under suction in order to separate the precipitated sodium chloride. From the filtrate, pure 1-butylbiguanide bis-(dichloroacetate) crystallizes. M.P.: 131°–132° C.

Example A

| Tablet formulation | | |
|---|---|---|
| 1-Butylbiguanide bis-(dichloroacetate) | 100 | mg |
| D-mannitol | 50 | mg |
| Corn starch | 95 | mg |
| Talc | 3.5 | mg |
| Magnesium stearate | 1.5 | mg |
| Total weight | 250.0 | mg |

We claim:

1. A compound of the formula

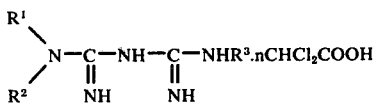

wherein $R^1$ is hydrogen, lower alkyl or lower alkenyl; $R^2$ is lower alkyl, aryl or aryl-lower alkyl; $R^3$ is hydrogen; and $n$ is 1 or 2.

2. A compound of the formula

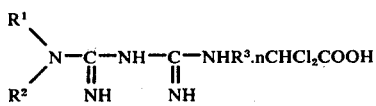

wherein $R^1$ is hydrogen or lower alkyl; $R^2$ is lower alkyl or phenyl-lower alkyl; $R^3$ is hydrogen; and $n$ is 1 or 2.

3. A compound in accordance with claim 1, 1,1-dimethylbiguanide bis-(dichloroacetate).

4. A compound in accordance with claim 1, 1-phenethylbiguanide bis-(dichloroacetate).

5. A compound in accordance with claim 1, 1-butylbiguanide bis-(dichloroacetate).